United States Patent
Irisawa et al.

(10) Patent No.: US 7,754,912 B2
(45) Date of Patent: Jul. 13, 2010

(54) POLYMERIZABLE COMPOUNDS

(75) Inventors: Masatomi Irisawa, Saitama (JP); Tatsunori Kobayashi, Saitama (JP); Mineki Hasegawa, Saitama (JP)

(73) Assignee: Adeka Corporation, Tokyo (JP)

( * ) Notice: Subject to any disclaimer, the term of this patent is extended or adjusted under 35 U.S.C. 154(b) by 77 days.

(21) Appl. No.: 12/096,762

(22) PCT Filed: Nov. 14, 2006

(86) PCT No.: PCT/JP2006/322597
§ 371 (c)(1),
(2), (4) Date: Jun. 9, 2008

(87) PCT Pub. No.: WO2007/080702
PCT Pub. Date: Jul. 19, 2007

(65) Prior Publication Data
US 2009/0247782 A1 Oct. 1, 2009

(30) Foreign Application Priority Data
Jan. 11, 2006 (JP) .............................. 2006-003724

(51) Int. Cl.
*C07C 69/76* (2006.01)
*C07C 69/86* (2006.01)
(52) U.S. Cl. ............................. 560/100; 560/80; 560/95
(58) Field of Classification Search ................... 560/76, 560/80, 83, 85, 95, 100; *C09K 19/38*
See application file for complete search history.

(56) References Cited

U.S. PATENT DOCUMENTS

| 2002/0158227 A1 | 10/2002 | Coates et al. | |
|---|---|---|---|
| 2007/0282087 A1* | 12/2007 | Irisawa et al. | 526/243 |
| 2009/0137761 A1* | 5/2009 | Irisawa et al. | 526/320 |

FOREIGN PATENT DOCUMENTS

| EP | 1 944 287 | | 7/2008 |
|---|---|---|---|
| JP | 11-116534 | | 4/1999 |
| JP | 11-130729 | | 5/1999 |
| JP | 11-513360 | | 11/1999 |
| JP | 3228348 | | 9/2001 |
| JP | 2002-265421 | | 9/2002 |
| JP | 2002-308831 | | 10/2002 |
| JP | 2002-308832 | | 10/2002 |
| JP | 2004-277488 | | 10/2004 |
| JP | 2005-15473 | | 1/2005 |
| JP | 2005-206579 | | 8/2005 |
| JP | 2005-208416 | | 8/2005 |
| JP | 2005-263789 | | 9/2005 |
| WO | 2006/049111 | | 5/2006 |
| WO | WO 2007052403 | * | 5/2007 |

OTHER PUBLICATIONS

International Search Report corresponding to International Application No. PCT/JP2006/322597.
European Patent Office issued an European Search Report dated Mar. 12, 2010, Application No. 06823371.7.

* cited by examiner

*Primary Examiner*—Shean C Wu
(74) *Attorney, Agent, or Firm*—Young & Thompson

(57) ABSTRACT

A novel polymerizable compound of the present invention is represented by the following general formula (I). Due to the presence of a reactive phenolic hydroxyl group at the end of the molecule, it can be reacted easily with various functional compounds and is useful as a monomer and an intermediate for various functional materials, especially as an intermediate for a polymerizable liquid crystal material.

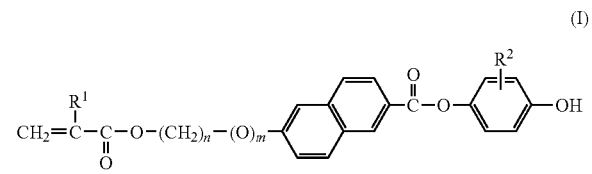

wherein $R^1$ is a hydrogen atom, a methyl group or a halogen atom; $R^2$ is an optionally substituted alkyl group having 1 to 6 carbon atoms, an optionally substituted alkoxy group having 1 to 6 carbon atoms, a halogen atom or a cyano group; an alkylene group of each of the alkyl and the alkoxy group may be interrupted by an unsaturated bond, an ether bond, a thioether bond or an ester bond; n is an integer from 0 to 14; and m is 0 or 1.

2 Claims, No Drawings

POLYMERIZABLE COMPOUNDS

TECHNICAL FIELD

The present invention relates to a novel polymerizable compound useful as a synthetic intermediate for a polymerizable liquid crystal compound and the like.

BACKGROUND ART

It is possible to prepare a polymeric material in which the oriented structure of liquid crystal molecules is fixed, by first orienting, in the liquid crystal state, a liquid crystal compound having a polymerizable functional group (hereafter, may also be referred to as a "polymerizable liquid crystal compound") or a liquid crystal composition containing at least one kind of the polymerizable liquid crystal composition (hereafter, may also be referred to as a "polymerizable liquid crystal composition"), and then irradiating the liquid crystal compound or the liquid crystal composition with an active energy ray such as ultraviolet light. The polymeric material thus obtained has anisotropies in physical properties such as a refractive index, a dielectric constant, magnetic susceptibility, an elastic modulus, a coefficient of thermal expansion and others, and thus may be used as an optical anisotropic material such as a retardation plate, a polarizing plate, a polarizing prism, a brightness improvement film, a low-pass filter, various light filters, a coating material for an optical fiber, and the like. With regard to the optical anisotropic material (polymer) obtained by polymerization, there are other important characteristics than anisotropies, including the rate of polymerization, transparency of the polymer, mechanical strength, coating properties, solubility, degree of crystallinity, shrinkage properties, permeability, hygroscopic degree, melting point, glass transition temperature, clearing point, chemical resistance, thermal resistance, and the like.

As the polymerizable liquid crystal compound, there has been proposed a polymerizable compound having a (meth) acryl group. Since the polymerizable liquid crystal compound whose polymerizable functional group is a (meth)acryl group has high polymerization reactivity and the obtained polymer shows high transparency, intensive investigations are conducted on application thereof as an optical anisotropic material (see, for example, Patent Documents 1 to 10).

In contrast, the present inventors have developed a polymerizable liquid crystal compound which provides an optical anisotropic material (polymer) which is excellent in the aforementioned characteristics and filed for the patent (Japanese Patent Application No. 2005-315699). The compound has excellent characteristics as a polymerizable liquid crystal material, and thus an intermediate which serves as a raw material is required.

Furthermore, a compound having a reactive functional group in addition to the polymerizable functional group is in demand as a monomer or an intermediate for various functional materials, because such compound is easy to react with various functional compounds.

Patent Document 1: Japanese Patent Laid-Open Publication No. H11-116534
Patent Document 2: Japanese Patent Application Laid-Open No. H11-130729
Patent Document 3: Japanese Patent Application Laid-Open No. H11-513360
Patent Document 4: Japanese Patent No. 3228348
Patent Document 5: Japanese Patent Laid-Open Publication No. 2005-015473
Patent Document 6: Japanese Patent Laid-Open Publication No. 2005-206579
Patent Document 7: Japanese Patent Laid-Open Publication No. 2002-265421
Patent Document 8: Japanese Patent Laid-Open Publication No. 2002-308831
Patent Document 9: Japanese Patent Laid-Open Publication No. 2002-308832
Patent Document 10: Japanese Patent Laid-Open Publication No. 2005-263789

DISCLOSURE OF THE INVENTION
Problems to be Solved by the Invention

Accordingly, an object of the present invention is to provide a novel polymerizable compound which is useful as an intermediate for a polymerizable liquid crystal material.

Means for Solving the Problems

The present inventors conducted diligent research in order to solve the above-mentioned problems and, as a result, found a novel polymerizable compound.

Specifically, the present invention is to provide a novel polymerizable compound represented by the following general formula (I).

[Formula 1]

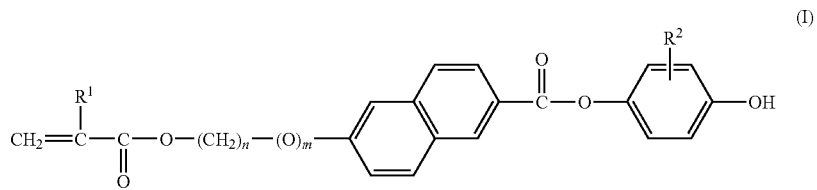

(I)

wherein $R^1$ is a hydrogen atom, a methyl group or a halogen atom; $R^2$ is an optionally substituted alkyl group having 1 to 6 carbon atoms, an optionally substituted alkoxy group having 1 to 6 carbon atoms, a halogen atom or a cyano group; an alkylene group of each of the alkyl and the alkoxy group may be interrupted by an unsaturated bond, an ether bond, a thioether bond or an ester bond; n is an integer from 0 to 14; and m is 0 or 1.

The present invention is also to provide the novel polymerizable compound which is a synthetic intermediate for a polymerizable liquid crystal compound.

BEST MODE FOR CARRYING OUT THE INVENTION

Hereafter, the novel polymerizable compound of the present invention, represented by the general formula (I), will be described in further detail.

In the general formula (I), examples of halogen atoms represented by $R^1$ and $R^2$ include a fluorine atom, a chlorine atom, a bromine atom, and an iodine atom; examples of $R^2$ that represents an optionally substituted alkyl group having 1 to 6 carbon atoms, include methyl, chloromethyl, trifluoromethyl, cyanomethyl, ethyl dichloroethyl, propyl, isopropyl, butyl, sec-butyl, tert-butyl, isobutyl, amyl, isoamyl, tert-amyl, hexyl, 2-hexyl, 3-hexyl, cyclohexyl, 1-methylcyclohexyl, and the like; examples of $R^2$ that represents an optionally substituted alkoxy group having 1 to 6 carbon atoms, include methoxy, chloromethoxy, trifluoromethoxy, cyanomethoxy, ethoxy, dichloroethoxy, propoxy, isopropoxy, butoxy, sec-butoxy, tert-butoxy, isobutoxy, amyloxy, isoamyloxy, tert-amyloxy, hexyloxy, cyclohexyloxy, and the like. The alkyl and alkoxy group taken as examples above may be interrupted by an unsaturated bond, ether bond, thioether bond, or ester bond.

As specific examples of the novel polymerizable compound of the present invention, represented by the foregoing general formula (I), there may be mentioned the following Compound Nos. 1 to 22. However, the present invention is not limited by the following compounds.

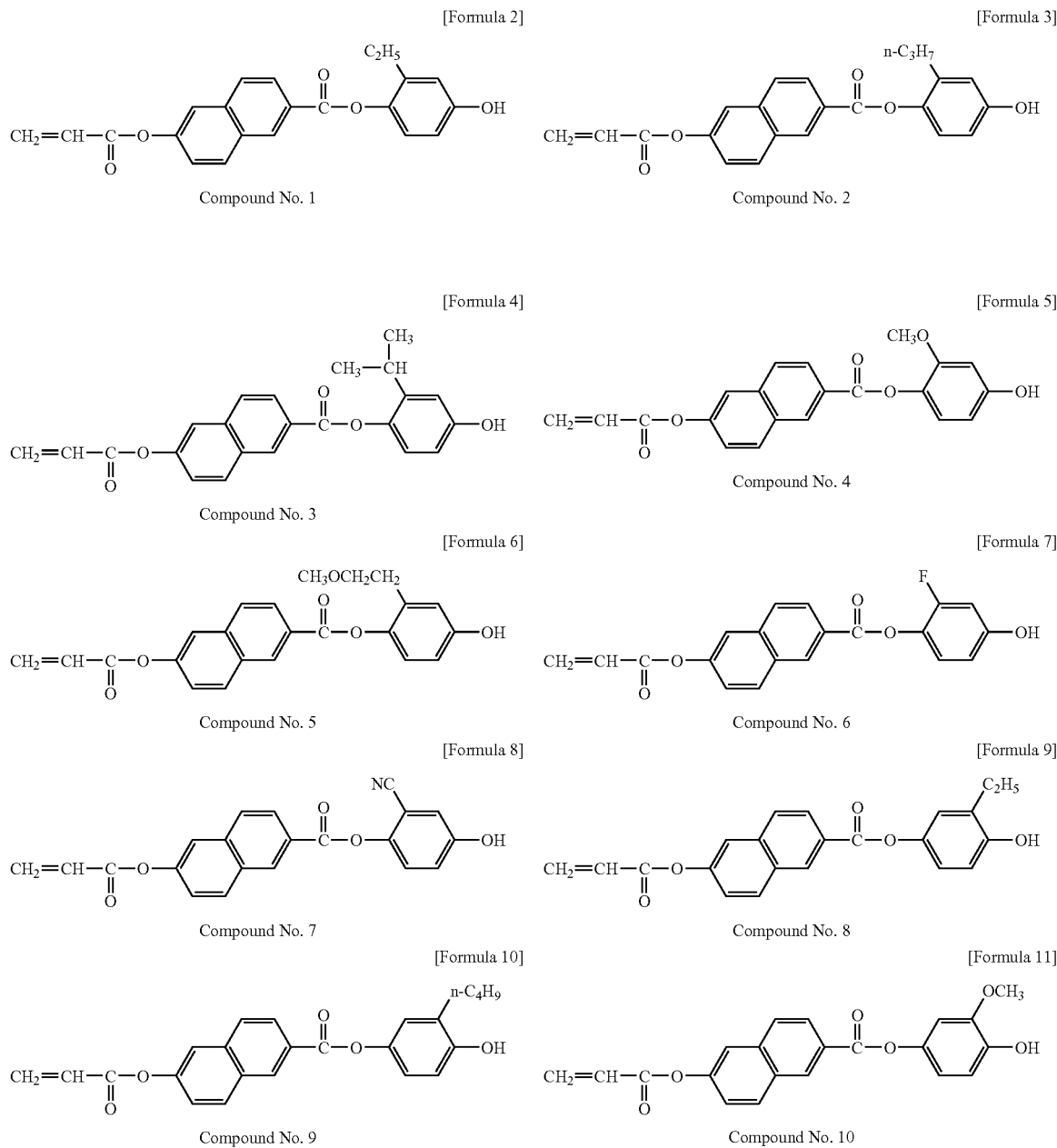

-continued
[Formula 12]
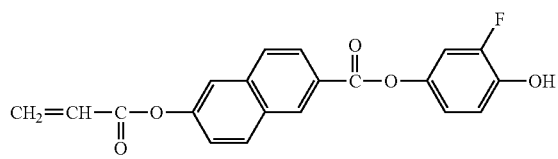
Compound No. 11
[Formula 13]
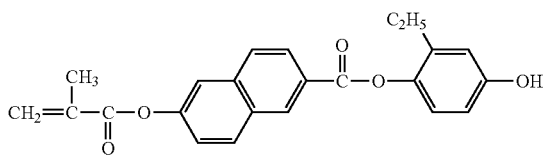
Compound No. 12
[Formula 14]
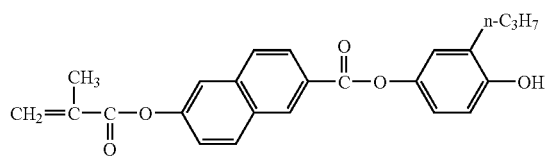
Compound No. 13
[Formula 15]
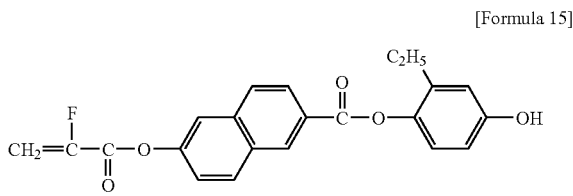
Compound No. 14
[Formula 16]
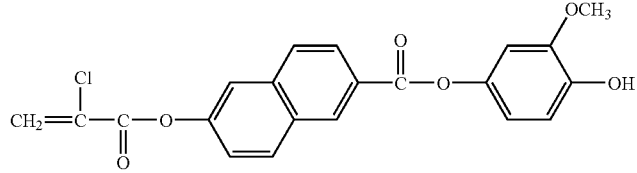
Compound No. 15
[Formula 17]
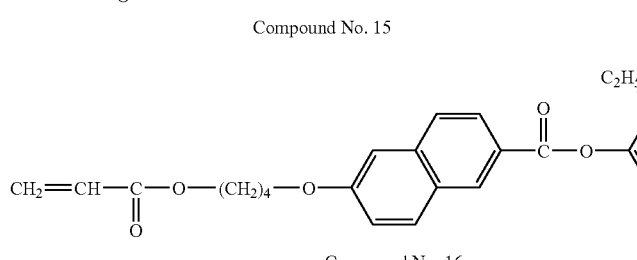
Compound No. 16
[Formula 18]
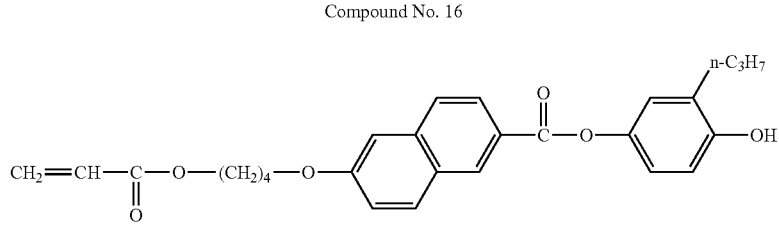
Compound No. 17
[Formula 19]
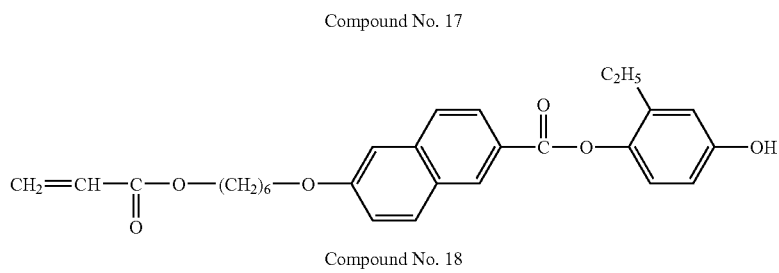
Compound No. 18
[Formula 20]
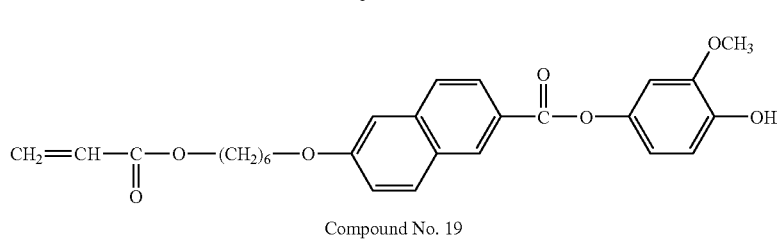
Compound No. 19

-continued

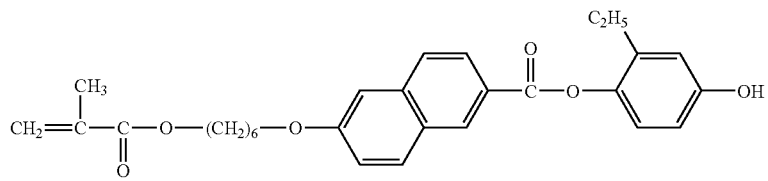

Compound No. 20

[Formula 21]

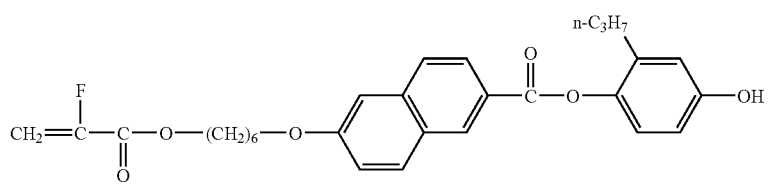

Compound No. 21

[Formula 22]

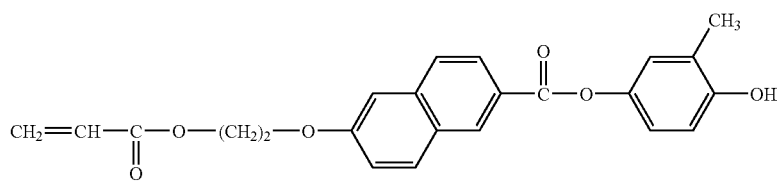

Compound No. 22

[Formula 23]

As regards the synthetic method for the compound of the present invention, represented by the general formula (I), there may be mentioned the following method.

As a raw material for the compound represented by the general formula (I), there may be mentioned compounds represented by the following general formulae (II) and (III).

[Formula 24]

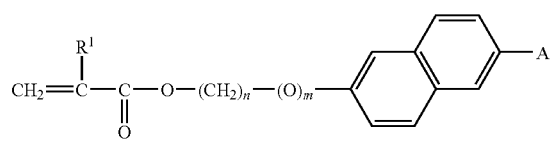

(II)

In the general formula (II), $R^1$ is a hydrogen atom, a methyl group, or a halogen atom; n is an integer from 0 to 14; A may be any one of groups which form an ester bond by an esterification reaction with an —OH group of a compound represented by the following general formula (III). Examples of A include a carboxyl group (—COOH), an acyl halide group (—COX, where X represents a halogen such as F, Cl, Br, I, and the like), a carboxylate group (—COOM, where M represents an alkali metal such as Na, K, Li, and the like), and, further include a p-toluenesulfonic acid ester (—CO—O-TS, where TS represents a tosyl group), a methanesulfonic acid ester (—CO—O-MS, where MS represents a mesyl group) and the like. $R^1$ and n in the general formula (II) correspond to $R^1$ and n of the compound represented by the general formula (I), respectively.

[Formula 25]

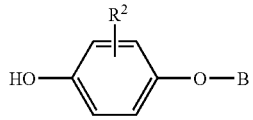

(III)

In the general formula (III), $R^2$ is an optionally substituted alkyl group having 1 to 6 carbon atoms, an optionally substituted alkoxy group having 1 to 6 carbon atoms, a halogen atom, or a cyano group, where an alkylene group in the alkyl and alkoxy group may be interrupted by an unsaturated bond, ether bond, thioether bond, or ester bond. $R^2$ in the general formula (III) corresponds to $R^2$ in the general formula (I).

In the general formula (III), B represents a protecting group for a phenolic hydroxyl group. The protecting group for the phenolic hydroxyl group may be one which is commonly used, with examples including a benzyl group, a p-methoxybenzyl (MPM) group, a trimethylsilyl (TMS) group, a tert-butyldimethylsilyl (TBDMS) group, a methoxymethyl (MOM) group, a methoxyethoxymethyl (MEM) group, and the like, and the benzyl group is especially preferable.

The reaction steps for preparing the compound represented by the general formula (I) include Step 1, where an esterification reaction is carried out between the compound represented by the general formula (II) and a compound represented by the general formula (III) to afford a compound represented by the general formula (IV). This is followed by Step 2, where the protecting group B is removed to afford a compound represented by the general formula (I). $R^1$ and $R^2$ in the general formula (IV) are derived from the general formulae (II) and (III), respectively, and correspond to those of the resultant compound represented by the general formula (I). B is derived from the general formula (III). The method for removing the protecting group in Step 2 may be selected appropriately depending on the nature of the protecting group.

[Formula 26]

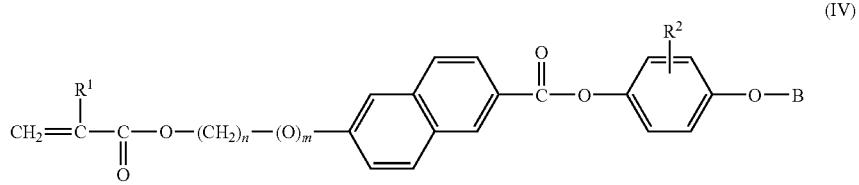

(IV)

The novel polymerizable compound of the present invention is characterized by the presence of a reactive phenolic hydroxyl group at the end of the molecule. By reacting this phenolic hydroxyl group with another compound, various polymerizable liquid crystal compounds may be obtained, which makes the novel polymerizable compound of the present invention useful as an intermediate for various polymerizable liquid crystal compounds.

Examples of the polymerizable liquid crystals to be obtained include those represented by the general formulae (V), (VI) and the like, but the polymerizable liquid crystals are not limited to these.

as an optical element such as a retardation film for a liquid crystal display, an optical compensation plate (retardation plate) for a liquid crystal display, an alignment layer for a liquid crystal display, a polarizing plate, a wide viewing angle plate, a reflection film, a color filter, a holographic element, a light polarizing prism, an optical head and the like; and as an optical anisotropic material for a low-pass filter, a brightness enhancement film, a polarizing beam splitter, and the like.

Furthermore, the novel polymerizable compound of the present invention has a reactive phenolic hydroxyl group at the end of the molecule and can be reacted easily with various functional groups. Thus, the novel polymerizable compound of the present invention is useful not only as an intermediate for the aforementioned liquid crystal compound but also as a monomer and an intermediate for various functional materials such as an optical anisotropic material, a color calibration

[Formula 27]

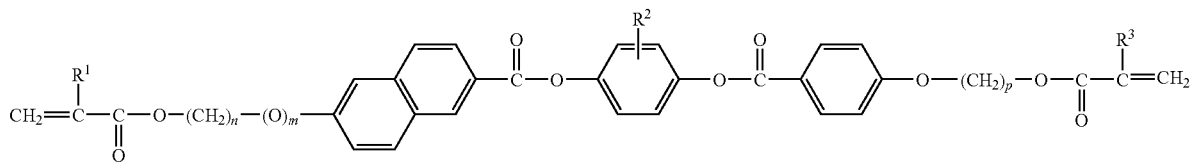

(V)

In the general formula (V), $R^1$, $R^2$ and n are the same as those in the compounds represented by the general formula (I); $R^3$ is a hydrogen atom, a methyl group or a halogen atom; m is 0 or 1; and p is an integer from 1 to 14.

plate, a wavelength conversion element, a nonlinear optical material, an organic semiconductor, an adhesive, a high-performance ink, a paint, a semiconductor resist, a color resist for a color filter, a photosensitive element, a membrane material

[Formula 28]

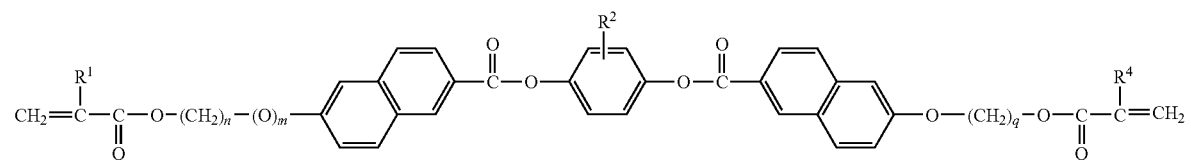

(V)

in the general formula (VI), $R^1$, $R^2$ and n are the same as those in the compounds represented by the general formula (I); $R^4$ is a hydrogen atom, a methyl group or a halogen atom; m is 0 or 1; and q is an integer from 1 to 14.

The polymerizable liquid crystal compound thus obtained can be polymerized or copolymerized into a (co)polymer (optical anisotropic material). The (co)polymer may be used with a high dielectric constant, various shielding materials, a resin substrate material, and the like.

EXAMPLES

Hereafter, the present invention will be further described in terms of Examples (Synthesis Examples). However, the present invention is not limited by these Examples.

In the following Examples (Synthesis Examples), the structure of a compound was confirmed by nuclear magnetic resonance ($^1$H-NMR) spectra, infrared (IR) absorption spectra, and the like.

Furthermore, the thermal transition behavior of the polymerizable liquid crystal compound was observed with DSC and a polarizing microscope. C stands for crystals, N for a nematic phase, and I for an isotropic liquid phase, respectively.

Example 1

Synthesis of Compound No. 2

Compound No. 2 of the present invention was synthesized according to the procedures of the following Steps 1 and 2.

<Step 1>

A benzyl ether compound was synthesized according to the following reaction equation and by the procedures described below.

[Formula 29]

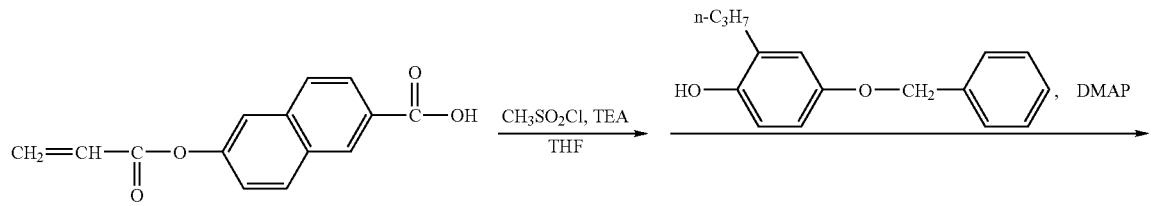

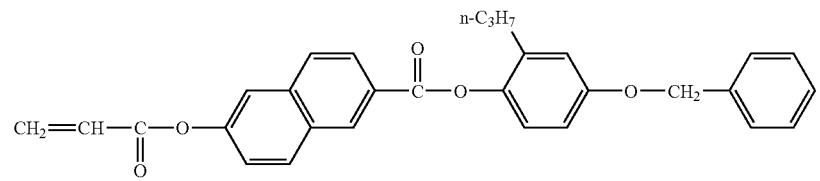

Specifically, 1.90 g (7.86 mmol) of 6-acryloyloxy-2-naphthoic acid was dissolved in 10 g of THF, to which 0.99 g (8.65 mmol) of methanesulfonyl chloride was added with ice-water bath cooling, and further 1.91 g (18.87 mmol) of triethylamine (TEA) was added dropwise. After stirring for 1 hour, 10 mg (0.08 mmol) of 4-dimethylaminopyridine (DMAP) was added, to which a solution of 2.00 g (8.25 mmol) of 4-benzyloxy-2-n-propylphenol dissolved in 7 g of THF was added dropwise. After stirring for 1 hour, the reaction mixture was allowed to warm to room temperature, the precipitates were removed by filtration, and the filtrate was washed with water. After removing the solvent by evaporation, the residue was purified by column chromatography (developing solvent: dichloromethane, $SiO_2$) and recrystallized from acetone. Thus the target benzyl ether was obtained as a white solid (2.27 g, 61.9% yield).

<Step 2>

Using the benzyl ether compound obtained in Step 1, Compound No. 2 was synthesized according to the following reaction equation and by the procedures described below.

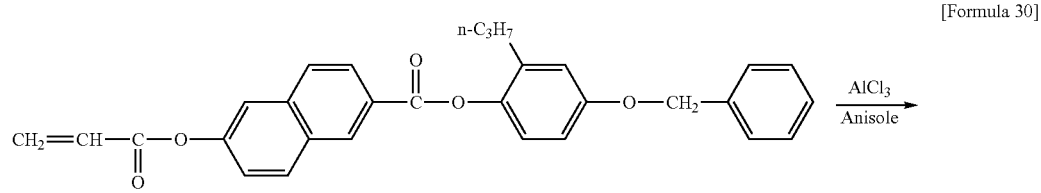

[Formula 30]

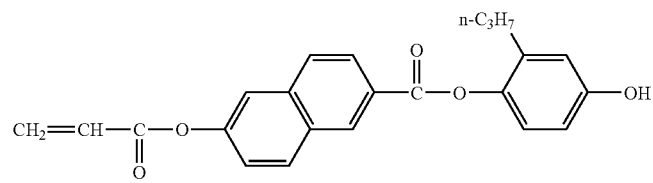

Specifically, 2.01 g (15.08 mmol) of anhydrous aluminum chloride was dissolved in 9 g of anisole, to which a solution of 2.27 g (4.87 mmol) of the benzyl ether compound obtained in Step 1 and dissolved in 9 g of anisole was added dropwise with ice-water bath cooling. After 1 hour of stirring, the reaction mixture was allowed to warm to room temperature and aqueous hydrochloric acid was added dropwise to dissolve the precipitate. The reaction mixture was washed with water and the solvent was removed by distillation. The residue was purified by column chromatography (developing solvent: ethyl acetate/toluene=1/5, $SiO_2$) and recrystallized from a mixed solvent, acetone/methanol, to afford a white solid (1.20 g, 65.6% yield).

Analysis of the white solid obtained confirmed that the white solid was the target material, Compound No. 2. The results of analysis are shown in the following.

(Results of Analysis)

(1) IR (KBr pellet method) ($cm^{-1}$)

3379, 2954, 2927, 2870, 1724, 1628, 1601, 1501, 1474, 1450, 1400, 1373, 1339, 1277, 1172, 1142, 1111, 1057

(2) $^1$H-NMR [$CDCl_3$] (ppm)

0.9 (t, 3H), 1.5-1.8 (m, 2H), 2.4-2.6 (t, 2H), 4.9 (s, 1H), 6.0-7.4 (m, 7H), 7.7-8.3 (m, 4H), 8.8 (s, 1H)

(3) Melting point 149.3° C. (DSC, 5° C./min)

Example 2

Synthesis of Polymerizable Liquid Crystals

Using Compound No. 2 obtained in Example 1 as an intermediate raw material, Polymerizable liquid crystal compound-1 was synthesized according to the following reaction equation.

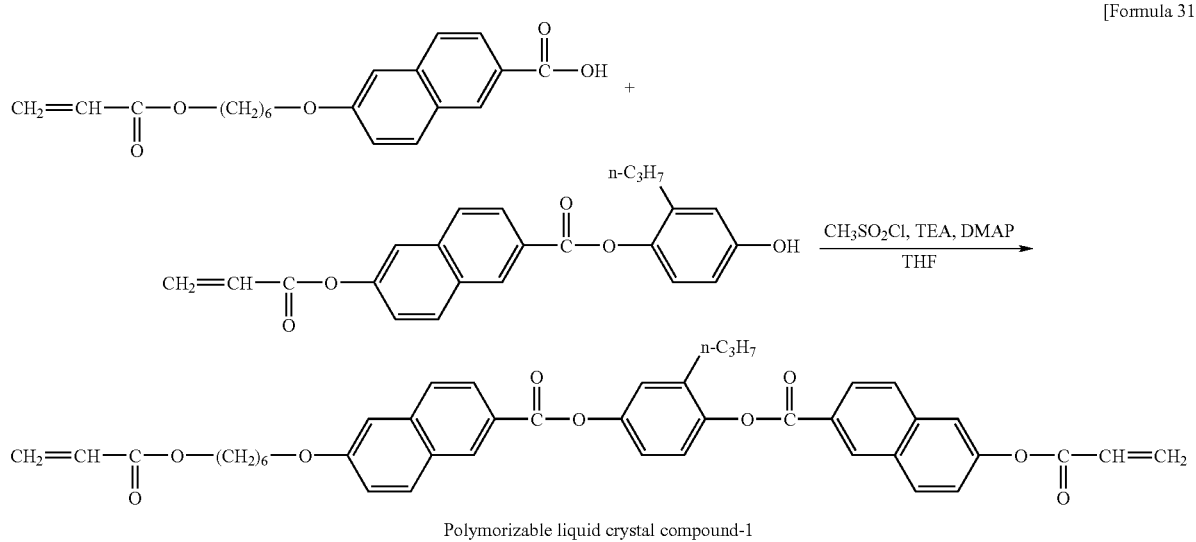

Polymorizable liquid crystal compound-1

Specifically, 1.04 g (3.04 mmol) of 6-(6-acryloyloxy-hexyloxy)-2-naphthoic acid was dissolved in 12 g of THF, to which 0.38 g (3.34 mmol) of methanesulfonyl chloride was added with ice-water bath cooling, and further 0.74 g (7.29 mmol) of triethylamine was added dropwise. After 1 hour of stirring, 4 mg (0.03 mmol) of DMAP was added, and a solution of 1.20 g (3.19 mmol) of Compound No. 2 obtained in Example 1 and dissolved in 8 g of THF was added dropwise. After 1 hour of stirring, the reaction mixture was allowed to warm to room temperature and precipitates were removed by filtration. The filtrate was washed with water and the solvent was removed by evaporation. The residue was purified by column-chromatography (developing solvent: ethyl acetate/toluene=1/5, $SiO_2$) and then, recrystallized from a mixed solvent of ethyl acetate/hexane to give a white solid (0.67 g, 31.5% yield). Analysis of the white solid obtained confirmed that the white solid was the target material, Polymerizable liquid crystal compound-1. The results of analysis are shown in the following.

(Results of Analysis)
(1) IR ($cm^{-1}$)
2936, 2866, 1624, 1474, 1404, 1339, 1273, 1246, 1200, 1169, 1150, 1065, 1022
(2) $^1$H-NMR (ppm)
0.9 (t, 3H), 1.5-1.9 (m, 10H), 2.6 (q, 2H), 3.9-4.3 (m, 4H), 5.7-6.6 (m, 6H), 7.1-7.5 (m, 6H), 7.7-8.3 (m, 7H), 8.7 (s, 1H), 8.9 (s, 1H)

(3) Thermal transition behavior

[Formula 32]

Thermal transition behavior

C: crystalline phase,
N: nematic phase,
I: isotropic liquid phase

INDUSTRIAL APPLICABILITY

The novel polymerizable compound of the present invention is useful as a synthetic intermediate, which can provide a polymerizable liquid crystal compound. Furthermore, due to the presence of a reactive phenolic hydroxyl group at the end of the molecule, the novel polymerizable compound of the present invention can be reacted easily with various functional compounds and are useful as a monomer and an intermediate for various functional materials.

The invention claimed is:

1. A novel polymerizable compound represented by the following general formula (I),

[Formula 1]

(I)

$$CH_2=C(R^1)-C(=O)-O-(CH_2)_n-(O)_m-\text{[naphthyl]}-C(=O)-O-\text{[phenyl}(R^2)\text{]}-OH$$

wherein $R^1$ is a hydrogen atom, a methyl group or a halogen atom; $R^2$ is an optionally substituted alkyl group having 1 to 6 carbon atoms, an optionally substituted alkoxy group having 1 to 6 carbon atoms, a halogen atom or a cyano group; an alkylene group of each of the alkyl and the alkoxy group may be interrupted by an unsaturated bond, an ether bond, a thioether bond or an ester bond; n is an integer from 0 to 14; and m is 0 or 1.

2. The novel polymerizable compound according to claim 1, which is a synthetic intermediate for a polymerizable liquid crystal compound.

* * * * *